(12) United States Patent
Ulrich et al.

(10) Patent No.: US 6,380,196 B1
(45) Date of Patent: Apr. 30, 2002

(54) DIHYDROBENZOFURANS

(75) Inventors: Wolf-Rüdiger Ulrich, Constance (DE); Geert Jan Sterk, Utrecht; Margaretha van der Mey, Rijnsburg, both of (NL)

(73) Assignee: Byk Gulden Lomberg Chemische Fabrik GmbH, Constance (DE)

( * ) Notice: Subject to any disclaimer, the term of this patent is extended or adjusted under 35 U.S.C. 154(b) by 0 days.

(21) Appl. No.: 09/554,088

(22) PCT Filed: Dec. 10, 1998

(86) PCT No.: PCT/EP98/08054

§ 371 Date: Aug. 3, 2000

§ 102(e) Date: Aug. 3, 2000

(87) PCT Pub. No.: WO99/31090

PCT Pub. Date: Jun. 24, 1999

(30) Foreign Application Priority Data

Dec. 15, 1997 (EP) ............................................. 97122039

(51) Int. Cl.⁷ ...................... A61K 31/495; A61K 31/50; C07D 237/00; C07D 237/30; A61P 11/00
(52) U.S. Cl. .......................... 514/248; 544/230; 544/237
(58) Field of Search ................................ 544/230, 237; 514/248

(56) References Cited

FOREIGN PATENT DOCUMENTS

| EP | 722936 | 7/1996 |
|----|--------|--------|
| WO | 91/12251 | 8/1991 |
| WO | 93/07146 | 4/1993 |
| WO | 94/12461 | 6/1994 |
| WO | 96/03399 | 2/1996 |

OTHER PUBLICATIONS

Nicholson et al., TIPS, 212, p. 19–27, 1991.*
"Novel Heterocyclic–Fused Pyridazinones as Potent and Selective Phosphodiesterase IV Inhibitors", Journal of Medicinal Chemistry 1997, V. Dal Piaz et al., vol. 40, 1417–1421.
"Novel Antiasthmatic Agents with dual Activities of Thromboxane $A_2$ Synthetase Inhibition and Bronchodialation", Journal of Medicinal Chemistry 1993, M. Yamaguchi et al., vol. 36, 4052–4060.

* cited by examiner

Primary Examiner—Brenda Coleman
(74) Attorney, Agent, or Firm—Jacobson Holman, PLLC

(57) ABSTRACT

Compounds of formula I,

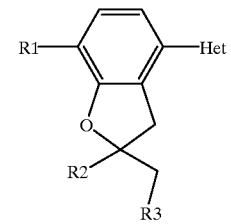

(I)

wherein Het represents a heterocycle having the meaning

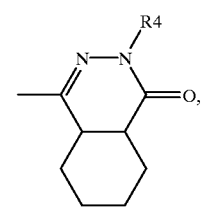

(a)

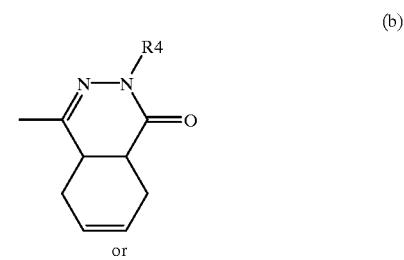

(b)

or

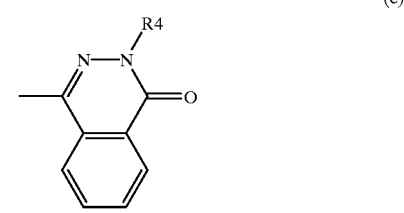

(c)

and R1, R2, R3 and R4 have the meanings as given in the description are novel effective bronchial therapeutics.

11 Claims, No Drawings

DIHYDROBENZOFURANS

This application is a national stage entry under 35 U.S.C. §371 of PCT/EP98/08054 filed Dec. 10, 1998.

FIELD OF APPLICATION OF THE INVENTION

The invention relates to novel compounds which are used in the pharmaceutical industry for the production of medicaments.

KNOWN TECHNICAL BACKGROUND

International Patent Applications WO91/12251 and WO93/07146 describe phthalazinones having bronchodilating and antiasthmatic properties. International Patent Application WO94/12461 describes 3-aryl-pyridazin-6-one derivatives as selective PDE4 inhibitors. European Patent Application EP 0722936 describes fused pyridazine compounds with cGMP-PDE inhibiting activity. In J. Med. Chem. 1993, 4052–4060 Yamaguchi et al. describe phthalazinones having thromboxane $A_2$ synthetase inhibitory and bronchodilatory activities.

DESCRIPTION OF THE INVENTION

It has been found that the phthalazinones described in greater detail below, which differ from the previously published compounds by a different substitution pattern have surprising and particularly advantageous properties.

The invention thus relates to compounds of the formula I

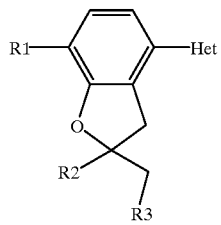

(I)

in which
R1 is 1–4C-alkoxy, 3–5C-cycloalkoxy, 3–5C-cycloalkylmethoxy, or 1–4C-alkoxy which is completely or predominantly substituted by fluorine,
R2 is 1–4C-alkyl and
R3 is hydrogen or 1–4C-alkyl,
or wherein
R2 and R3 together and with inclusion of the two carbon atoms, to which they are bonded, form a spirolinked 5-, 6- or 7-membered hydrocarbon ring, optionally interrupted by an oxygen or sulphur atom,
Het represents a heterocycle having the meaning

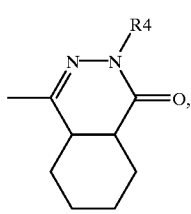

(a)

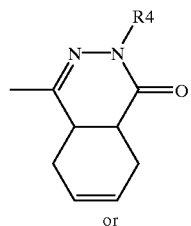

(b)

or

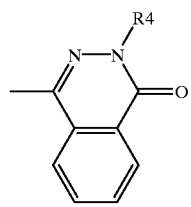

(c)

wherein
R4 is R5, —$C_mH_{2m}$—R6 or —$C_pH_{2p}$—Y—Ar
R5 is hydrogen, 1–8C-alkyl, 3–10C-cycloalkyl, 3–7C-cycloalkylmethyl, 7–10C-polycycloalkyl an unsubstituted phenyl or pyridyl radical or a phenyl radical substituted by R51 and/or R52, in which
R51 is 1–4C-alkyl, 1–4C-alkoxy, carboxyl, 1–4C-alkoxycarbonyl, cyano, nitro, halogen, hydroxyl, amino, mono- or di-1–4C-alkylamino, imidazolyl or tetrazolyl, and
R52 is 1–4C-alkyl, 1–4C-alkoxy, nitro or halogen,
R6 is hydroxyl, halogen, nitro, cyano, carboxyl, 1–4C-alkoxycarbonyl, amino, mono- or di-1–4C-alkylamino, aminocarbonyl or mono- or di-1–4C-alkylaminocarbonyl,
Y is O (oxygen), S (sulphur) or a covalent bond,
Ar is an unsubstituted phenyl, naphthyl, pyridyl, pyrazinyl, pyridazinyl, pyrimidinyl, quinazolinyl, quinoxalinyl, cinnolinyl, isoquinolyl, quinolyl, purinyl, benzimidazolyl, benzotriazolyl, benzoxazolyl, coumarinyl, imidazolyl, pyrazolyl, oxazolyl or pyrrolyl radical or a phenyl radical substituted by R7 and/or R8, in which
R7 is hydroxyl, halogen, nitro, cyano, 1–4C-alkyl, 1–4C-alkoxy, carboxyl, carboxy-1–4C-alkyl, 1–4C-alkoxycarbonyl, amino, mono- or di-1–4C-alkylamino, aminocarbonyl, mono- or di-1–4C-alkylaminocarbonyl, 1–4C-alkylcarbonylamino, imidazolyl or tetrazolyl,
R8 is halogen, nitro, 1–4C-alkyl or 1–4C-alkoxy,
m is an integer from 1 to 4,
p is an integer from 1 to 4,
and the salts of these compounds.

1–4C-Alkyl is a straight-chain or branched alkyl radical having 1 to 4 carbon atoms. Examples are the butyl, isobutyl, sec-butyl, tert-butyl, propyl, isopropyl, ethyl and methyl radicals.

1–4C-Alkoxy is a radical which, in addition to the oxygen atom, contains a straight-chain or branched alkyl radical having 1 to 4 carbon atoms. Alkoxy radicals having 1 to 4 carbon atoms which may be mentioned in this context are, for example, the butoxy, isobutoxy, sec-butoxy, tert-butoxy, propoxy, isopropoxy, ethoxy and methoxy radicals.

3–5C-Cycloalkoxy stands for cyclopropyloxy, cyclobutyloxy and cyclopentyloxy.

3–5C-Cycloalkylmethoxy stands for cyclopropylmethoxy, cyclobutylmethoxy and cyclopentylmethoxy.

1–4C-Alkoxy which is completely or predominantly substituted by fluorine is, for example, the 2,2,3,3,3-pentafluoropropoxy, the perfluoroethoxy, the 1,2,2-trifluoroethoxy and in particular the 1,1,2,2-tetrafluoroethoxy, the 2,2,2-trifluoroethoxy, the trifluoromethoxy and the difluoromethoxy radical, of which the difluoromethoxy radical is preferred.

As spiro-linked 5-, 6- or 7-membered hydrocarbon rings, optionally interrupted by an oxygen or sulphur atom, may be mentioned the cyclopentane, cyclohexane, cycloheptane, tetrahydrofuran, tetrahydropyran and the tetrahydrothiophen ring.

According to the invention, the group Het is represented by a heterocycle having the meaning a, b or c, of which the heterocycles having the meaning a or b are preferred.

Possible groups —$C_pH_{2p}$—, —$C_mH_{2m}$— are straight chain or branched groups. Examples which may be mentioned are the butylene, isobutylene, sec-butylene, tert-butylene, propylene, isopropylene, ethylene and the methylene group.

1–8C-Alkyl is a straight-chain or branched alkyl radical having 1 to 8 carbon atoms. Examples are the octyl, isooctyl (6-methylheptyl), heptyl, isoheptyl (5-methylhexyl), hexyl, isohexyl (4-methylpentyl), neohexyl (3,3-dimethylbutyl), pentyl, isopentyl (3-methylbutyl), neopentyl (2,2-dimethylpropyl), butyl, isobutyl, sec-butyl, tert-butyl, propyl, isopropyl, ethyl and methyl radicals.

3–10C-Cycloalkyl stands, for example, for cyclopropyl, cyclopentyl, cyclohexyl and cycloheptyl.

3–7C-Cycloalkylmethyl stands for a methyl radical, which is substituted by one of the above-mentioned 3–7C-cycloalkyl radicals.

7–10C-polycycloalkyl stands for 7–10C-bicycloalkyl or 7–10C-tricycloalkyl groups, such as for example, bornyl, norbornyl or adamantyl.

Halogen within the meaning of the present invention is bromine, chlorine and fluorine.

1–4C-Alkoxycarbonyl is a carbonyl group to which one of the above-mentioned 1–4C-alkoxy radicals is bonded. Examples are the methoxycarbonyl [$CH_3O$—$C(O)$—] and the ethoxycarbonyl [$CH_3CH_2O$—$C(O)$—] radical.

Mono- or Di-1–4C-alkylamino radicals contain in addition to the nitrogen atom, one or two of the above-mentioned 1–4C-alkyl radicals. Preferred are the di-1–4C-alkylamino radicals, especially the dimethylamino, the diethylamino and the diisopropylamino radical.

Mono- or Di-1–4C-alkylaminocarbonyl radicals contain in addition to the carbonyl group one of the above-mentioned mono- or di-1–4C-alkylamino radicals. Examples which may be mentioned are the N-methyl- the N,N-dimethyl-, the N-ethyl-, the N-propyl-, the N,N-diethyl- and the N-isopropylamino-carbonyl radical.

An 1–4C-Alkylcarbonylamino radical is, for example, the propionylamino [$C_3H_7C(O)NH$—] and the acetylamino radical [$CH_3C(O)NH$—].

Carboxy-1–4C-alkyl radical are, for example, the carboxymethyl (—$CH_2COOH$) and the carboxyethyl (—$CH_2CH_2COOH$) radicals.

Suitable salts for compounds of the formula I—depending on substitution—are all acid addition salts or all salts with bases. Particular mention may be made of the pharmacologically tolerable salts with the inorganic and organic acids and bases customarily used in pharmacy. Those suitable are, on the one hand, water-soluble and water-insoluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3-hydroxy-2-naphthoic acid, the acids being employed in salt preparation—depending on whether a mono- or polybasic acid is concerned and depending on which salt is desired—in an equimolar quantitative ratio or one differing therefrom.

On the other hand, salts with bases are—depending on substitution—also suitable. As examples of salts with bases are mentioned the lithium, sodium, potassium, calcium, aluminium, magnesium, titanium, ammonium, megiumine or guanidinium salts, here, too, the bases being employed in salt preparation in an equimolar quantitative ratio or one differing therefrom.

Pharmacologically intolerable salts, which can be obtained, for example, as process products during the preparation of the compounds according to the invention on an industrial scale, are converted into pharmacologically tolerable salts by processes known to the person skilled in the art.

According to expert's knowledge the compounds of the invention as well as their salts may contain, e.g. when isolated in crystalline form, varying amounts of solvents. Included within the scope of the invention are therefore all solvates and in particular all hydrates of the compounds of formula I as well as all solvates and in particular all hydrates of the salts of the compounds of formula I.

Compounds of the formula I to be emphasized are those, in which

R1 is 1–4C-alkoxy, 3–5C-cycloalkoxy, 3–5C-cycloalkylmethoxy, or 1–4C-alkoxy which is completely or predominantly substituted by fluorine, R2 is 1–4C-alkyl and R3 is hydrogen or 1–4C-alkyl, or wherein R2 and R3 together and with inclusion of the two carbon atoms, to which they are bonded, form a spirolinked cyclopentane, cyclohexane, tetrahydrofuran or tetrahydropyran ring, Het represents a heterocycle having the meaning

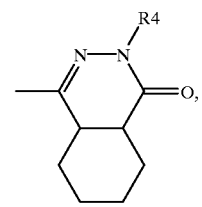

(a)

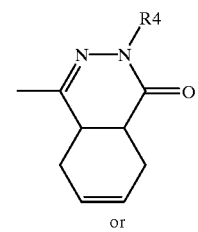

(b)

or

-continued (c)

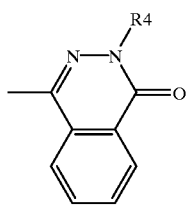

wherein

R4 is R5, —C$_m$H$_{2m}$—R6 or —C$_p$H$_{2p}$—Y—Ar,

R5 is hydrogen, 1–6C-alkyl, 3–7C-cycloalkyl, 3–7C-cycloalkylmethyl, bornyl, norbornyl, adamantyl or an unsubstituted or by R51 substituted phenyl radical, in which R51 is 1–4C-alkyl, 1–4C-alkoxy, carboxyl, 1–4C-alkoxycarbonyl or halogen, R6 is hydroxyl, halogen, carboxyl or 1–4C-alkoxycarbonyl, Y is O (oxygen) or a covalent bond, Ar is an unsubstituted phenyl, pyridyl, purinyl, benzimidazolyl, benzotriazolyl, imidazolyl, pyrazolyl, or pyrrolyl radical, or a phenyl radical substituted by R7, in which R7 is halogen, nitro, cyano, 1–4C-alkyl, 1–4C-alkoxy, carboxyl, carboxy-1–2C-alkyl, 1–4C-alkoxy-carbonyl or tetrazolyl, m is an integer from 1 to 4, p is an integer from 1 to 4, and the salts of these compounds.

Compounds of the formula I which are particularly to be emphasized are those, in which R1 is 1–2C-alkoxy or 1–2C-alkoxy which is completely or predominantly substituted by fluorine, R2 is 1–4C-alkyl and R3 is hydrogen or 1–4C-alkyl, or wherein R2 and R3 together and with inclusion of the two carbon atoms, to which they are bonded, form a spirolinked cyclopentane or cyclohexane ring, Het represents a heterocycle having the meaning (a)

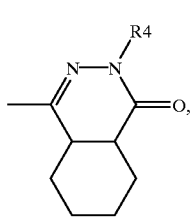

(b)

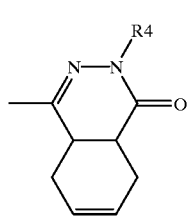

-continued or (c)

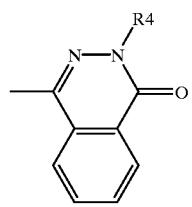

wherein

R4 is R5, —C$_m$H$_{2m}$—R6 or —C$_p$H$_{2p}$—Y—Ar,

R5 is hydrogen, 3–7C-cycloalkyl, 3–7C-cycloalkylmethyl, adamantyl or an unsubstituted or by R51 substituted phenyl radical, in which R51 is carboxyl or 1–4C-alkoxycarbonyl, R6 is hydroxyl or halogen, Y is O (oxygen) or a covalent bond, Ar is an unsubstituted phenyl, pyridyl, imidazolyl or purinyl radical, or a phenyl radical substituted by R7, in which R7 is cyano, 1–4C-alkyl, 1–4C-alkoxy, carboxyl, 1–4C-alkoxycarbonyl or tetrazolyl, m is an integer from 1 to 4, p is an integer from 1 to 4, and the salts of these compounds.

One embodiment of the compounds of the formula I particularly to be emphasized are those, in which R1 is 1–2C-alkoxy or 1–2C-alkoxy which is completely or predominantly substituted by fluorine, R2 is 1C-alkyl and R3 is hydrogen or 1–4C-alkyl, or wherein R2 and R3 together and with inclusion of the two carbon atoms, to which they are bonded, form a spirolinked cyclopentane or cyclohexane ring, Het represents a heterocycle having the meaning (a)

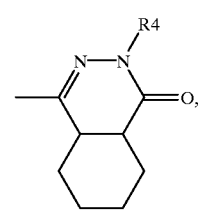

(b)

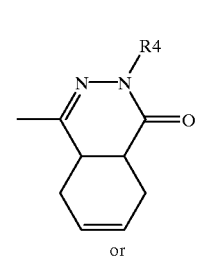

or

-continued

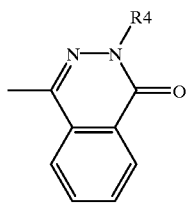
(c)

wherein
R4 is R5, —$C_mH_{2m}$—R6 or —$C_pH_{2p}$—Y—Ar,
R5 is hydrogen, 3–7C-cycloalkyl, 3–7C-cycloalkylmethyl, adamantyl or phenyl,
R6 is hydroxyl or halogen,
Y is O (oxygen) or a covalent bond,
Ar is an unsubstituted phenyl or pyridyl radical, or a phenyl radical substituted by R7, in which
R7 is cyano, 1–4C-alkyl, 1–4C-alkoxy, carboxyl, 1–4C-alkoxycarbonyl or tetrazolyl,
m is an integer from 1 to 4,
p is an integer from 1 to 4,
and the salts of these compounds.

Preferred compounds of the formula I are those, in which
R1 is methoxy or difluoromethoxy,
R2 is methyl,
R3 is hydrogen,
or wherein
R2 and R3 together and with inclusion of the two carbon atoms, to which they are bonded, form a spirolinked cyclopentane ring,
Het represents a heterocycle having the meaning

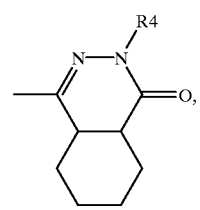
(a)

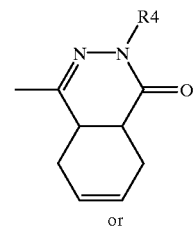
(b)

or

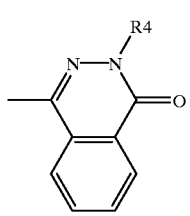
(c)

wherein
R4 is R5, —$C_mH_{2m}$—R6 or —$C_pH_{2p}$—Y—Ar,
R5 is hydrogen, 3–7C-cycloalkyl or an unsubstituted or by R51 substituted phenyl radical, in which
R51 is carboxyl,
R6 is hydroxyl or halogen,
Y is O (oxygen) or a covalent bond,
Ar is an unsubstituted phenyl, pyridyl, imidazolyl or purinyl radical, or a phenyl radical substituted by R7, in which
R7 is cyano, carboxyl or tetrazolyl,
m is an integer from 1 to 4,
p is an integer from 1 to 4,
and the salts of these compounds.

One embodiment of the preferred compounds of the formula I are those compounds in which
R1 is methoxy or difluoromethoxy,
R2 is methyl,
R3 is hydrogen,
or wherein
R2 and R3 together and with inclusion of the two carbon atoms, to which they are bonded, form a spirolinked cyclopentane ring,
Het represents a heterocycle having the, meaning (a)

(b)

or (c)

wherein
R4 is R5, —$C_mH_{2m}$—R6 or —$C_pH_{2p}$—Y—Ar,
R5 is hydrogen, 3–7C-cycloalkyl or phenyl,
R6 is hydroxyl or halogen,
Y is O (oxygen) or a covalent bond,
Ar is an unsubstituted phenyl, pyridyl, imidazolyl or purinyl radical, or a phenyl radical substituted by R7, in which
R7 is cyano, carboxyl or tetrazolyl,
m is an integer from 1 to 4,

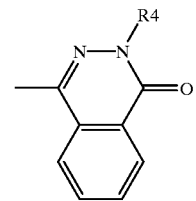

p is an integer from 1 to 4, and the salts of these compounds.

Especially preferred compounds of formula I are those, in which

R1 is methoxy,

R2 is methyl,

R3 is hydrogen, or wherein

R2 and R3 together and with inclusion of the two carbon atoms, to which they are bonded, form a spirolinked cyclopentane ring, Het represents a heterocycle having the meaning

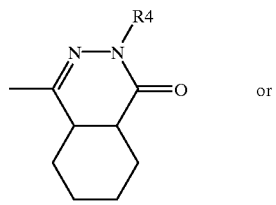

(a)

or

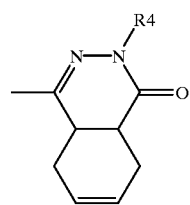

(b)

wherein

R4 is R5, —$C_mH_{2m}$—R6 or —$C_pH_{2p}$—Y—Ar,

R5 is hydrogen, cyclopentyl, cycloheptyl, phenyl or p-carboxyphenyl,

R6 is hydroxyl,

Y is O (oxygen) or a covalent bond,

Ar is an unsubstituted phenyl, pyridyl, imidazolyl or purinyl radical, or a phenyl radical substituted by R7, in which R7 is cyano, carboxyl or tetrazoyl, m is an integer from 1 to 4, p is an integer from 1 to 4, and the salts of these compounds.

One embodiment of the especially preferred compounds of formula I are those compounds in which R1 is methoxy, R2 is methyl, R3 is hydrogen, or wherein R2 and R3 together and with inclusion of the two carbon atoms, to which they are bonded, form a spirolinked cyclopentane ring, Het represents a heterocycle having the meaning

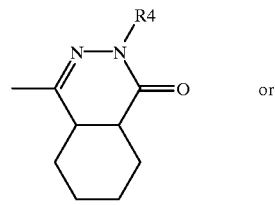

(a)

or

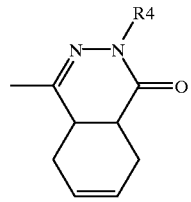

(b)

wherein

R4 is R5, —$C_mH_{2m}$—R6 or —$C_pH_{2p}$—Y—Ar,

R5 is hydrogen, cyclopentyl, cycloheptyl or phenyl,

R6 is hydroxyl,

Y is O (oxygen) or a covalent bond,

Ar is an unsubstituted phenyl, pyridyl, imidazolyl or purinyl radical, or a phenyl radical substituted by R7, in which R7 is cyano, carboxyl or tetrazoyl, m is an integer from 1 to 4, p is an integer from 1 to 4, and the salts of these compounds.

Exemplary compounds according to the invention are listed in the following tables:

TABLE 1

Compounds of the formula I, in which Het represents a heterocycle having the meaning (a), (b) or (c), R4 is cycloheptyl, and the following further substituents meanings:

| R1 | R2 | R3 |
|---|---|---|
| $OCH_3$ | $CH_3$ | H |
| $OC_2H_5$ | $CH_3$ | H |
| $OCF_2H$ | $CH_3$ | H |
| $OCF_3$ | $CH_3$ | H |
| $OCH_3$ | $C_2H_5$ | $CH_3$ |
| $OC_2H_5$ | $C_2H_5$ | $CH_3$ |
| $OCF_2H$ | $C_2H_5$ | $CH_3$ |
| $OCF_3$ | $C_2H_5$ | $CH_3$ |
| $OCH_3$ | $CH_2CH_2CH_2$ | |
| $OC_2H_5$ | $CH_2CH_2CH_2$ | |
| $OCF_2H$ | $CH_2CH_2CH_2$ | |
| $OCF_3$ | $CH_2CH_2CH_2$ | |
| $OCH_3$ | $CH_2CH_2CH_2CH_2$ | |
| $OC_2H_5$ | $CH_2CH_2CH_2CH_2$ | |
| $OCF_2H$ | $CH_2CH_2CH_2CH_2$ | |
| $OCF_3$ | $CH_2CH_2CH_2CH_2$ | |
| $OCH_3$ | $CH_2$—O—$CH_2$ | |
| $OC_2H_5$ | $CH_2$—O—$CH_2$ | |
| $OCF_2H$ | $CH_2$—O—$CH_2$ | |
| $OCF_3$ | $CH_2$—O—$CH_2$ | |
| $OCH_3$ | $CH_2CH_2$—O | |
| $OC_2H_5$ | $CH_2CH_2$—O | |
| $OCF_2H$ | $CH_2CH_2$—O | |
| $OCF_3$ | $CH_2CH_2$—O | |
| $OCH_3$ | $CH_2CH_2$—O—$CH_2$ | |

TABLE 1-continued

Compounds of the formula I, in which Het represents a heterocycle having the meaning (a), (b) or (c), R4 is cycloheptyl, and the following further substituents meanings:

| R1 | R2 | R3 |
|---|---|---|
| $OC_2H_5$ | $CH_2CH_2$—O—$CH_2$ | |
| $OCF_2H$ | $CH_2CH_2$—O—$CH_2$ | |
| $OCF_3$ | $CH_2CH_2$—O—$CH_2$ | |

TABLE 2

Compounds of the formula I, in which Het represents a heterocycle having the meaning (a), (b) or (c), R4 is cyclopentyl, and the following further substituents meanings:

| R1 | R2 | R3 |
|---|---|---|
| $OCH_3$ | $CH_3$ | H |
| $OC_2H_5$ | $CH_3$ | H |
| $OCF_2H$ | $CH_3$ | H |
| $OCF_3$ | $CH_3$ | H |
| $OCH_3$ | $C_2H_5$ | $CH_3$ |
| $OC_2H_5$ | $C_2H_5$ | $CH_3$ |
| $OCF_2H$ | $C_2H_5$ | $CH_3$ |
| $OCF_3$ | $C_2H_5$ | $CH_3$ |
| $OCH_3$ | $CH_2CH_2CH_2$ | |
| $OC_2H_5$ | $CH_2CH_2CH_2$ | |
| $OCF_2H$ | $CH_2CH_2CH_2$ | |
| $OCF_3$ | $CH_2CH_2CH_2$ | |
| $OCH_3$ | $CH_2CH_2CH_2CH_2$ | |
| $OC_2H_5$ | $CH_2CH_2CH_2CH_2$ | |
| $OCF_2H$ | $CH_2CH_2CH_2CH_2$ | |
| $OCF_3$ | $CH_2CH_2CH_2CH_2$ | |
| $OCH_3$ | $CH_2$—O—$CH_2$ | |
| $OC_2H_5$ | $CH_2$—O—$CH_2$ | |
| $OCF_2H$ | $CH_2$—O—$CH_2$ | |
| $OCF_3$ | $CH_2$—O—$CH_2$ | |
| $OCH_3$ | $CH_2CH_2$—O | |
| $OC_2H_5$ | $CH_2CH_2$—O | |
| $OCF_2H$ | $CH_2CH_2$—O | |
| $OCF_3$ | $CH_2CH_2$—O | |
| $OCH_3$ | $CH_2CH_2$—O—$CH_2$ | |
| $OC_2H_5$ | $CH_2CH_2$—O—$CH_2$ | |
| $OCF_2H$ | $CH_2CH_2$—O—$CH_2$ | |
| $OCF_3$ | $CH_2CH_2$—O—$CH_2$ | |

TABLE 3

Compounds of the formula I, in which Het represents a heterocycle having the meaning (a), (b) or (c), R4 is benzyl, and the following further substituents meanings:

| R1 | R2 | R3 |
|---|---|---|
| $OCH_3$ | $CH_3$ | H |
| $OC_2H_5$ | $CH_3$ | H |
| $OCF_2H$ | $CH_3$ | H |
| $OCF_3$ | $CH_3$ | H |
| $OCH_3$ | $C_2H_5$ | $CH_3$ |
| $OC_2H_5$ | $C_2H_5$ | $CH_3$ |
| $OCF_2H$ | $C_2H_5$ | $CH_3$ |
| $OCF_3$ | $C_2H_5$ | $CH_3$ |
| $OCH_3$ | $CH_2CH_2CH_2$ | |
| $OC_2H_5$ | $CH_2CH_2CH_2$ | |
| $OCF_2H$ | $CH_2CH_2CH_2$ | |
| $OCF_3$ | $CH_2CH_2CH_2$ | |
| $OCH_3$ | $CH_2CH_2CH_2CH_2$ | |
| $OC_2H_5$ | $CH_2CH_2CH_2CH_2$ | |
| $OCF_2H$ | $CH_2CH_2CH_2CH_2$ | |
| $OCF_3$ | $CH_2CH_2CH_2CH_2$ | |
| $OCH_3$ | $CH_2$—O—$CH_2$ | |
| $OC_2H_5$ | $CH_2$—O—$CH_2$ | |
| $OCF_2H$ | $CH_2$—O—$CH_2$ | |

TABLE 3-continued

Compounds of the formula I, in which Het represents a heterocycle having the meaning (a), (b) or (c), R4 is benzyl, and the following further substituents meanings:

| R1 | R2 | R3 |
|---|---|---|
| $OCF_3$ | $CH_2$—O—$CH_2$ | |
| $OCH_3$ | $CH_2CH_2$—O | |
| $OC_2H_5$ | $CH_2CH_2$—O | |
| $OCF_2H$ | $CH_2CH_2$—O | |
| $OCF_3$ | $CH_2CH_2$—O | |
| $OCH_3$ | $CH_2CH_2$—O—$CH_2$ | |
| $OC_2H_5$ | $CH_2CH_2$—O—$CH_2$ | |
| $OCF_2H$ | $CH_2CH_2$—O—$CH_2$ | |
| $OCF_3$ | $CH_2CH_2$—O—$CH_2$ | |

The compounds of formula I are chiral compounds with a chiral center in the dihydrofuran-ring, if the substituents —R2 and —$CH_2R3$ are not identical. However, preferred are those compounds, in which the substituents —R2 and —$CH_2R3$ are identical or together and with inclusion of the carbon atom to which they are bonded form a spiro-connected 5-, 6- or 7-membered hydrocarbon ring. Additional chiral centers exist in the positions 4a and 8a in those cases, in which Het represents a heterocycle having the meaning (a) or (b):

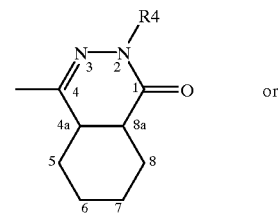

(a)

or

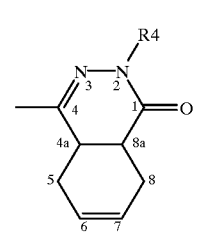

(b)

Therefore the invention includes all conceivable pure diastereomers and pure enantiomers, as well as all mixtures thereof independent from the ratio, including the racemates. Preferred are those compounds, in which the hydrogen atoms in the positions 4a and 8a are cis-configurated. Especially preferred are in this connection those compounds, in which the absolute configuration (according to the rules of Cahn, Ingold and Prelog) is S in the position 4a and R in the position 8a. Racemates can be split up into the corresponding enantiomers by methods known by the person skilled in the art. Preferably the racemic mixtures are seperated into two diastereomers with the help of an optical active separation agent on the stage of the cyclohexanecarboxylic acids (for example, starting compound B) or the 1,2,3,6-tetrahydrobenzoic acids (for example, starting compounds A and D). As separation agents may be mentioned, for example, optical active amines such as the (+)- and (−)-forms of aphenylethylamine and ephedrine, or the optical active alkaloids cinchonine, cinchonidine and brucine.

The invention further relates to a process (see scheme 1) for the preparation of compounds of formula I and their salts.

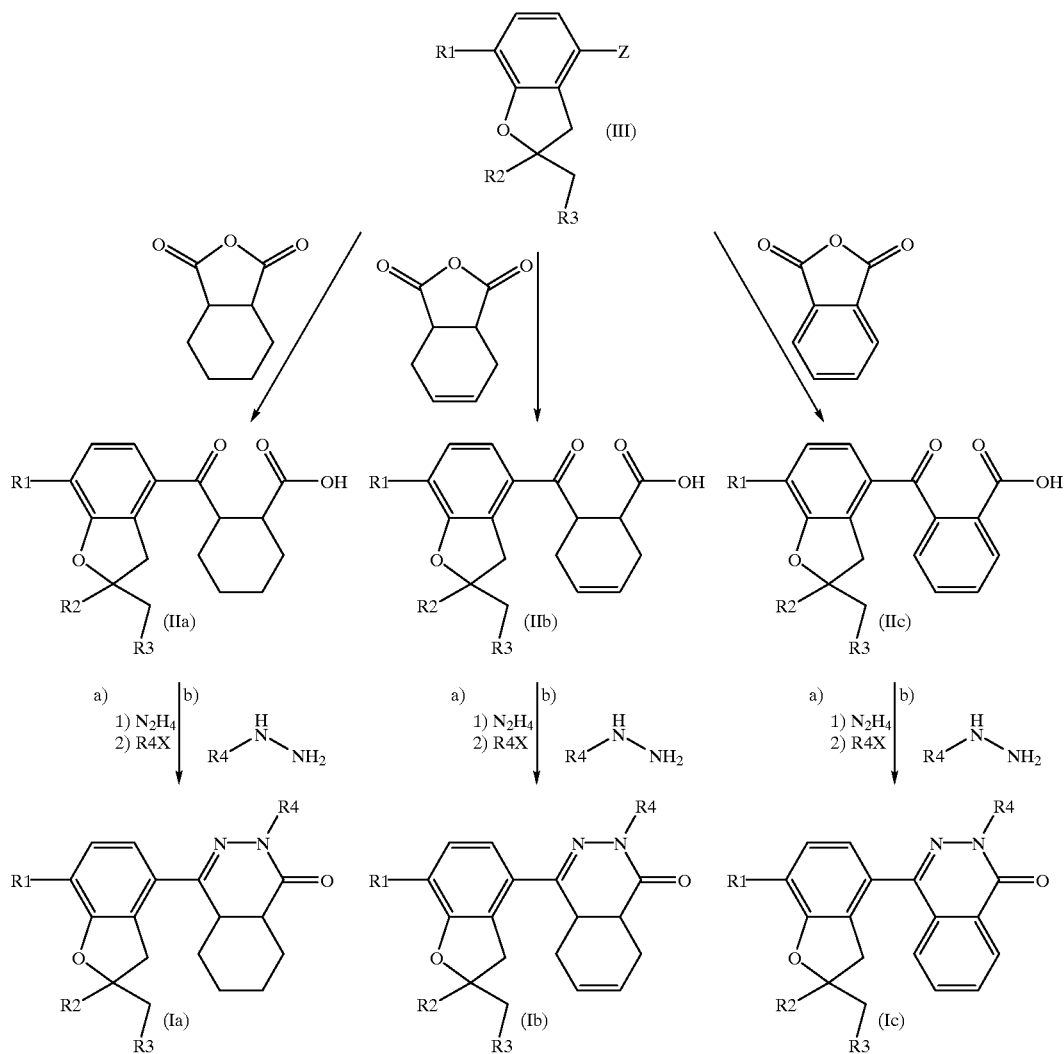

Scheme 1

The Process Comprises
a) reacting keto acids of formula IIa (IIb, IIc) or one of their reactive derivatives, in which R1, R2 and R3 have the above-mentioned meanings in a first step with hydrazine hydrate to compounds of formula Ia (Ib, Ic), in which R1, R2 and R3 have the above-mentioned meanings and R4 stands for hydrogen (H).

If desired, these compounds can be reacted with alkylating agents of formula R4-X, in which R4 has the above-mentioned meanings [exception: R4 does not represent hydrogen (H)] and X represents a leaving group to give further compounds of formula I, in which R1, R2, R3 and R4 have the above-mentioned meanings [exception: R4 does not represent hydrogen (H)].

b) reacting, alternatively to procedure a), keto acids of formula IIa (IIb, IIc) or one of their reactive derivatives, in which R1, R2 and R3 have the above-mentioned meanings with suitable hydrazine derivates of formula R4-NH-NH$_2$, in which R4 has the above-mentioned meanings [exception: R4 does not represent hydrogen (H)], to give compounds of the formula Ia (Ib, Ic), in which R1, R2, R3 and R4 have the above-mentioned meanings [exception: R4 does not represent hydrogen (H)].

The conversion of the keto acids of formula IIa (IIb, IIc) or one of their reactive derivatives with hydrazine hydrate [according to procedure a)] respectively with suitable hydrazine-derivates of the formula R4-NH-NH$_2$ [according to procedure b)] is advantageously carried out with one to five equivalents of hydrazine hydrate respectively the suitable hydrazine derivates of formula R4-NH-NH$_2$, which simultaneously can be used as solvent. More suitable is, however, to use an additional appropriate solvent. As inert solvents are preferably used alcohols such as methanol, ethanol, isopropanol, n-butanol, isoamylalcohol, glycols and their ethers such as ethylene glycol, diethylene glycol, ethylene glycol monomethyl or monoethyl ether, carboxylic acids such as formic acid, acetic or propionic acid, suitable mixtures of the above-mentioned solvents, as well as mixtures with water, for example aqueous ethanol, further ethers, especially water soluble ethers such as tetrahydrofuran, dioxane or ethylene glycol dimethylether; further toluene or benzene, especially when the method of azeotropic destilation is used to remove the reaction water.

The reaction temperatures are suitably between 0 and 200° C., preferably between 20 and 100° C.; the reaction times are preferably between 1 and 48 hours.

Suitable reactive derivatives of the keto acids of formula IIa (IIb, IIc) which may be mentioned in this context are, for example, esters, especially methyl and ethyl esters, nitrils and acid halides, such as acid chlorides or acid bromides. They can be prepared, for example, starting from the corresponding keto acids of formula IIa (IIb, IIc), by methods which are known by the person skilled in the art.

The conversion of compounds of formula Ia (Ib, Ic), in which R1, R2 and R3 have the above-mentioned meanings and R4 represents hydrogen (H) with alkylating agents of the formula R4-X, in which R4 has the above-mentioned meanings [with the exception of hydrogen(H)] and X represents a suitable leaving group, is carried out in a manner, which is known by a person skilled in the art.

In a first step, the hydrogen atom (H) of the NH-group of the compounds of formula Ia (Ib, Ic), in which R4 represents a hydrogen atom (H) is removed by a base such as, for example, potassium carbonate, sodium hydroxide, sodium hydride, sodium methanolate, sodium ethanolate or buthyllithium in a suitable inert solvent such as dimethylformamide, dimethylsulfoxide, tetrahydrofuran or diethylether. The bases are preferably used in more than an equimolar ratio.

The alkylation is then carried out by adding an appropriate alkylating agent of the formula R4-X.

Examples of suitable leaving groups X which may be mentioned are halogen atoms, especially chlorine, or hydroxyl groups activated by esterification (for example with p-toluenesulfonic acid).

Suitable alkylating agents of the formula R4-X are for example iodomethane, bromoethane, 1-bromo-propane, 2-bromopropane, 3-bromopentane, cyclopentylbromide, bromomethylcyclohexane, cycloheptylbromide, 4-chloromethylbenzoic acid, 3-bromomethylbenzoic acid, 4-chloromethylphenylacetic acid, 2-methoxybenzy chloride, 3-methoxybenzylchloride, 4-methoxybenzylchloride, 3,5-dimethoxybenzyl-chloride, 2-chlorobenzylchloride, 2-picolylchloride, 3-picolylchloride, 4-picolylchloride and 2-bromoethyl-benzene.

Examples for suitable hydrazine-derivates of formula R4-NH-NH$_2$ are methylhydrazine, 2-hydroxyethylhydrazine, phenylhydrazine, benzylhydrazine, 4-tert-butylhydrazine, 2-bromophenylhydrazine, 4-chlorophenylhydrazine, 4-fluorophenylhydrazine, 2,4-dichlorophenylhydrazine, 4-chloro-o-tolylhydrazine, 2,5-dimethylphenylhydrazine, 2,4-dinitrophenylhydrazine, 4-methoxyphenylhydrazine, 3-nitrophenyl-hydrazine, p-tolylhydrazine and 4-hydrazinobenzoic acid.

Keto acids of the formula IIa (IIb, IIc), in which R1, R2 and R3 have the above-mentioned meanings can, for example, be prepared from compounds of the formula III, in which R1, R2 and R3 have the above-mentioned meanings and Z represents hydrogen (H) by Friedel-Crafts acylation with hexahydrophthalic anhydride, 1,2,3,6-tetrahydrophthalic anhydride or phthalic anhydride. The Friedel-Crafts acylation is carried out in a manner which in known by the skilled person (for example as described in M. Yamaguchi et al., J. Med. Chem. 36: 4052–4060, 1993) in presence of a suitable catalyst, such as for example, AlCl$_3$, ZnCl$_2$, FeCl$_3$ or iodine, in an appropriate inert solvent, such as methylene chloride or nitrobenzene or another inert solvent such as diethyl ether, preferably at raised temperature, especially at the boiling point of the solvent being used.

Alternatively, the compounds of formula IIa (IIb, IIc), in which R1, R2 and R3 have the above-mentioned meanings, can be prepared from compounds of the formula III, in which RI R2 and R3 have the above-mentioned meanings and Z represents a halogen atom through reaction with hexahydrophthalic anhydride, 1,2,3,6-tetrahydro-phthalic anhydride, or phthalic anhydride.

The reaction is carried out in a manner which is known by a person skilled in the art, for example a) by activating compounds of formula III, in which R1, R2, R3 and Z have the above-mentioned meanings, by a lithium/halogen exchange reaction at low temperatures (preferably at −60 to −100° C.) in an appropriate inert solvent such as tetrahydrofuran or diethylether, preferably under an atmosphere of inert gas, followed by reaction of the lithiated compounds the above-mentioned anhydrides, or b) by converting compounds of formula III, in which R1, R2, R3 and Z have the above-mentioned meanings, in a suitable inert solvent such as, for example, tetrahydrofuran or diethyl ether into the corresponding Grignard compounds of formula III, in which Z represents MgCl, MgBr or MgI followed by reaction of the Grignard compounds with the above-mentioned anhydrides.

Compounds of formula III, in which R1, R2 and R3 have the above-mentioned meanings and Z represents a hydrogen (H) or halogen atom, are known or can be prepared according to the reaction scheme 2.

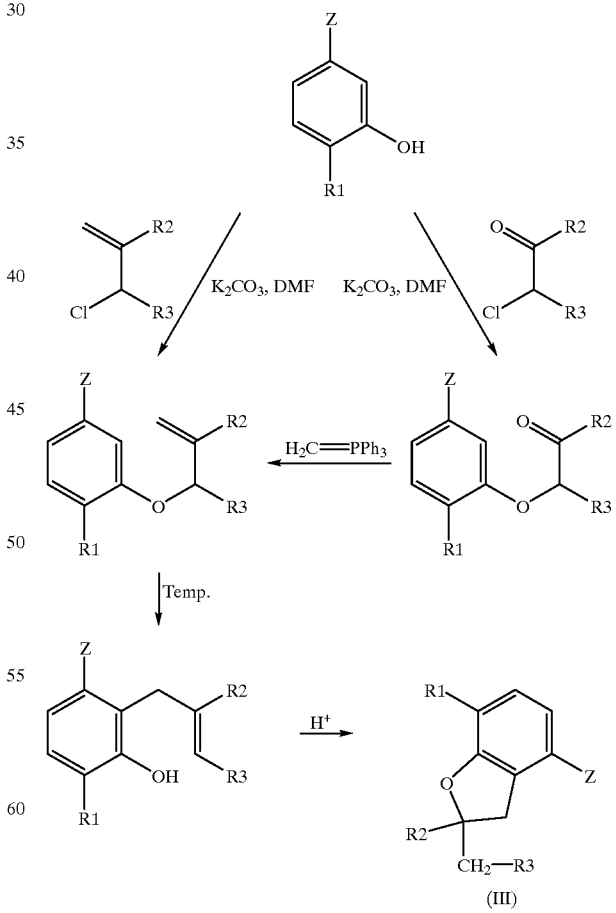

Scheme 2

By way of example, the preparation of compounds of the formula III is described in the following examples under "starting compounds". The preparation of further compounds of formula III can be carried out in an analogous manner.

Additionally, it is possible to convert one functional group of a compound of formula I (Ia, Ib, Ic) to another functional group by customary methods and reactions.

Thus, if desired, compounds of formula I with suitable functional groups can be converted into further compounds of formula I.

For instance, compounds of formula I, in which R4 comprises an ester can be converted by acidic or alkaline saponification to the corresponding carboxylic acid.

Suitably, the conversions are carried out analogous to methods which are familiar per se to the person skilled in the art, for example, in the manner which is described in the following examples.

The substances according to the invention are isolated and purified in a manner known per se, e.g. by destining off the solvent in vacuo and recrystallizing the residue obtained from a suitable solvent or subjecting it to one of the customary purification methods, such as column chromatography on a suitable support material.

Salts are obtained by dissolving the free compound in a suitable solvent, e.g. in a chlorinated hydrocarbon, such as methylene chloride or chloroform, or a low molecular weight aliphatic alcohol (ethanol, isopropanol) which contains the desired acid or base, or to which the desired acid or base is then added. The salts are obtained by filtering, reprecipitating, precipitating with a non-solvent for the addition salt or by evaporating the solvent. Salts obtained can be converted by basification or by acidifying into the free compounds which, in turn, can be converted into salts. In this manner, pharmacologically non-tolerable salts can be converted into pharmacologically tolerable salts.

The following examples illustrate the invention in greater detail, without restricting it. As well, further compounds of formula I, of which the preparation is explicitly not described, can be prepared in an analogous way or in a way which is known by a person skilled in the art using customary preparation methods.

In the examples stand M.p. for melting point, min for minutes, THF for tetrahydrofuran and DMF for N,N-dimethylformamide.

The compounds, which are mentioned in the examples as well as their salts are preferred compounds of the invention.

EXAMPLES

Final Products 1. (cis)-4-(2,3-Dihydro-7-methoxybenzofuran-2-spiro-1'-cyclopentan-4-yl)-4a,5,8,8a-tetrahydro-2H-phthalazin-1-one A solution of 8 g of compound A and 10 g of hydrazine hydrate in 100 ml of ethanol refluxed for 3 hours. After evaporating the solvent, the residue was partitioned between ethyl acetate and aqueous sodium carbonate. The organic layer was dried over magnesium sulfate and concentrated under reduced pressure upon which the compound crystallized. M. p. 193–194° C.

2. (cis)-4-(2,3-Dihydro-7-methoxybenzofuran-2-spiro-1'-cyclopentan-4-yl)4a,5,6,7,8,8a-hexahydro-2H-phthalazin-1-one Prepared from compound B and hydrazine hydrate as described for compound 1. Crystallization from methanol. M. p. 185–186° C.

3. 4-(2,3-Dihydro-7-methoxybenzofuran-2-spiro-1'-cyclopentan-4-yl)-2H-phthalazin-1-one The title compound can be prepared from compound C and hydrazine hydrate as described for compound 1.

4. (cis)-4-(2,3-Dihydro-2,2-dimethyl-7-methoxybenzofuran-4-yl)-4a,5,8,8a-tetrahydro-2H-phthalazin-1-one Prepared from compound D and hydrazine hydrate as described for compound 1. Crystallization from ethyl acetate/petroleum ether (60–80° C.). M. p. 242° C.

5. (cis)-4-(2,3-Dihydro-7-methoxybenzofuran-2-spiro-1'-cyclopentane-4-yl)-2-cyclopentyl-4a,5,8,8a-tetrahydro-2H-phthalazin-1-one Prepared from compound 1 and cyclopentyl bromide as described for compound 11. The compound was purified by chromatography [ethyl acetate/petroleum ether (60–95° C.), 1:6] and crystallized from diethyl ether/petroleum ether (60–95° C.). M. p. 162° C.

6. (cis)-4-(2,3-Dihydro-7-methoxybenzofuran-2-spiro-1'-cyclopentan-4-yl)-2-cycloheptyl-4a,5,8,8a-tetrahydro-2H-phthalazin-1-one Prepared from compound 1 and cycloheptyl bromide as described for compound 11. The compound was purified by chromatography [ethyl acetatelpetroleum ether (60–95° C.), 1:4] and crystallized from diethyl ether/petroleum ether (60–95° C.). M. p. 135° C.

7. (cis)-4-(2,3-Dihydro-7-methoxybenzofuran-2-spiro-1'-cyclopentan-4-yl)-2-benzyl-4a,5,8,8a-tetrahydro-2H-phthalazin-1-one Prepared from compound 1 and benzyl chloride as described for compound 11. The compound was purified by chromatography [ethyl acetate/petroleum ether (60–95° C.), 1:4] and crystallized from diethyl ether/petroleum ether (60–95° C.). M. p. 99–100° C.

8. (cis)-4-(2.3-Dihydro-7-methoxybenzofuran-2-spiro-1'-cyclopentan-4-yl)-2-phenyl-4a,5,8,8a-tetrahydro-2H-phthalazin-1-one A solution of 1 g of phenylhydrazine and 1.5 g of compound A in 1-butanol was refluxed for 18 h and subsequently evaporated. The residue was purified by chromatography (ethyl acetate/petroleum ether (60–95° C.), 1:4). Crystallization from diethyl ether/petroleum ether (60–95° C.). M. p. 127–128° C.

9. (4aS, 8aR)-4-(2,3-Dihydro-7-methoxybenzofuran-2-spiro-1'-cyclopentan-4-yl)-4a,5,6,7,8,8a-hexahydro-2H-phthalazin-1-one A solution of 10 mmol of (−)-ephedrine in 20 ml of ethanol was added to a solution of 20 mmol of compound B in 20 ml of ethanol. The resulting mixture was left for 18 h at room temperature and the precipitate was filtered off and dried (4 mmol). M. p. 148–149° C.

$^1$H-NMR experiments in CDCl$_3$ confirmed the presence of one enantiomere in >98% purity.

The precipitate obtained above was partioned between ethyl acetate and 1N hydrochloric acid. The organic layer was dried over magnesium sulfate and evaporated. The residue was dissolved in ethanol and, after the addition of 6 mmol of hydrazine hydrate, refluxed for 3 hours. After evaporating the solvent, the compound was crystallized from methanol. The enantiomeric purity of the compound was confirmed by $^1$H-NMR experiments in CDCl$_3$ using Europium tris[3-(heptafluoropropylhydroxymethylene)-(+)-camphorate], which showed an enatiomeric purity of >98%. M. p. 87–88° C.

10. (4aR, 8aS)-4-(2,3-Dihydro-7-methoxybenzofuran-2-spiro-1'-cyclopentan-4-yl)-4a,5,6,7,8,8a-hexahydro-2H-phthalazin-1-one Prepared from compound B and (+)-ephedrine as described for compound 9. Melting point of the (+)-ephedrine salt: M. p. 151–152° C. M. p. (title compound) 87–88° C.

11. (cis)-4-(2,3-Dihydro-7-methoxybenzofuran-2-spiro-1'-cyclopentan-4-yl)-2-(4-carboxybenzyl)-4a,5,6,7,8,8a-hexahydro-2H-phthalazin-1-one To a solution of 1 g of compound 2 in 30 ml of N-methylpyrrolidinone, 2.11 g of a 70% suspension of sodium hydride in mineral oil was added. After stirring this mixture for ten minutes, 0.5 g of 4-(chloromethyl)benzoic acid was added and the resulting mixture stirred for 2 hours. After dilution with ethyl acatate, the mixture was washed twice with 1N hydrochloric acid. The organic layer was dried over magnesium sulfate and evaporated. The residue was purified by chromatography (ethyl acetate) and crystallized from ethyl acetate. M. p. 213–215° C.

12. (cis)-4-(2,3-Dihydro-7-methoxybenzofuran-2-spiro-1'-cyclopentan-4-yl)-2-(4-pyridylmethyl)-4a,5,6,7,8,8a-hexahydro-2H-phthalazin-1-one-hydrochloride Prepared from compound 2 and 4-picolyl chloride hydrochloride as described for compound 11. The reaction mixture was diluted with 200 ml of ethyl acetate and washed twice with 1M sodium hydroxide. The compound was purified by chromatography (ethyl acetate) and crystallized as the hydrochloride from diethyl ether. M. p. 196–198° C.

13. (cis)-4-(2,3-Dihydro-7-methoxybenzofuran-2-spiro-1'-cyclopentan-4-yl)-2-cycloheptyl-4a,5,6,7,8,8a-hexahydro-2H-phthalazin-1-one Prepared from compound 1 and cycloheptyl bromide as described for compound 11. The compound was purified by chromatography [ethyl acetate/petroleum ether (60–95° C.), 1:5] and crystallized from petroleum ether (60–95° C.). M. p.118–120° C.

14. (cis)-4-(2,3-Dihydro-7-methoxybenzofuran-2-spiro-1'-cyclopentan-4-yl)-2-benzyl-4a,5,6,7,8,8a-hexahydro-2H-phthalazin-1-one Prepared from compound 1 and benzyl chloride as described for compound 11. The compound was purified by chromatography [ethyl acetate/petroleum ether (60–95° C.), 1:4] and crystallized from petroleum ether (60–95° C.)ethyl acetate. M. p. 104–106° C.

15. (cis)-4-(2,3-Dihydro-7-methoxybenzofuran-2-spiro-1'-cyclopentan-4-yl)-2-benzyl-phthalazin-1-one Prepared from compound 3 and benzyl chloride as described for compound 11. The compound was purified by chromatography [ethyl acetate/petroleum ether (60–80° C.), 1:6]. M. p. 167° C.

16. (cis)-4-(2,3-Dihydro-7-methoxybenzofuran-2-spiro-1'-cyclopentan-4-yl)-2-cycloheptyl-phthalazin-1-one Prepared from compound 3 and cycloheptyl bromide as described for compound 11. Crystallized from methanol. M. p. 210° C.

17. (cis)-4-(2,3-Dihydro-7-methoxybenzofuran-2-spiro-1'-cyclopentan-4-yl-2-hydroxyethyl-4a,5,8,8a-tetrahydro-2H-phthalazin-1-one A solution of 8 g of compound A and 10 g of 2-hydroxyethylhydrazine in 150 ml of 1-butanol was refluxed for 18 hours. After evaporating the solvent, the residue was dissolved in diethyl ether and this solution was washed with water. After drying over magnesium sulfate and concentrating under reduced pressure, the compound crystallized. M.p. 129–130° C.

18. (cis)-4-(2,3-Dihydro-7-methoxybenzofuran-2-spiro-1'-cyclopentan-4-yl)-2-bromoethyl-4a,5,8,8a-tetrahydro-2H-phthalazin-1-one A solution 1.92 g of Br$_2$ in CH$_2$Cl$_2$ was added to a solution of 3.1 g of triphenylphosphine in CH$_2$Cl$_2$ at 0° C., followed by the addition of a solution of 4.6 g of compound 17 in CH$_2$Cl$_2$. The resulting solution was stirred for 2 hours at room temperature and subsequently washed with diluted hydrochloric acid (2x) and aqueous sodium carbonate. Crystallisation from methanol (2x). M.p. 143–145° C.

19. (cis)-4-(2,3-Dihydro-7-methoxybenzofuran-2-spiro-1'-cyclopentan-4-yl)-2-[2-(4-cyanophenoxy)ethyl]-4a,5,8,8a-tetrahydro-2H-phthalazin-1-one A mixture of 2,0 g of compound 18, 2 g of 4-hydroxybenzonitrile and 2 g of K$_2$CO$_3$ in 50 ml of DMF was heated for 2 hours at 110° C. After cooling to room temperature, 100 ml of water and 150 ml of diethyl ether was added to the reaction mixture. The ether layer was dried over MgSO$_4$ and evaporated. The residue was purified by chromatography and the compound crystallised from ether. M.p. 127–128° C.

20. (cis)-4-(2,3-Dihydro-7-methoxybenzofuran-2-spiro-1'-cyclopentan-4-yl)-2-[2-(4-tetrazol phenoxy)ethyl]-4a,5,8,8a-tetrahydro-2H-phthalazin-1-one A solution of 1.2 g of compound 19, 1,1 g of NaN$_3$ and 0.9 g of NH$_4$Cl in 50 ml of DMF was heated for 10 hours at 120° C. After cooling to room temperature, the mixture was evaporated and the residue partitioned between diluted hydrochloric acid and ethyl acetate. The organic layer was dried over magnesium sulfate and evaporated. The compound was crystallized from ethyl acetate. M.p. 123–126° C.

21. (cis)-4-(2,3-Dihydro-7-methoxybenzofuran-2-spiro-1'-cyclopentan-4-yl)-2-[4-(bromo-1-butyl)]-4a,5,8,8a-tetrahydro-2H-phthalazin-1-one 6.4 g of 1,4-dibromobutane was added to a solution of 3.5 g of compound 1 and 0.4 g of a 60% suspension of sodium hydride in 50 ml of 1-methyl-2-pyrrolidinone at room temperature. After 2 hours, 150 ml of water was added to the reaction mixture and the resulting mixture extracted with diethyl ether. The ether was evaporated in vacuo and the residue purified by chromatography [petroleum ether (60–80° C.): ethyl acetate, 6:1]. M.p. 86–88° C.

22. (cis)-4(2,3-Dihydro-7-methoxybenzofuran-2-spiro-1'-cylopentan-4-yl)-2-[4-(imidazol-1yl)-1-butyl]-4a,5,8,8a-tetrahydro-phthalazin-1-one A mixture of 1.65 g of compound 21, 0.5 g of imidazole and 0.9 g of $K_2CO_3$ in 20 ml of dimethylformamide was heated at 90° C. for 3 hours. After evaporating the solvent, 100 ml of water was added to the residue and this mixture was extracted with ethyl acetate. The organic layer was dried over $MgSO_4$ and evaporated. Purified by chromatography (ethyl acetate) and crystallised from diethyl ether. M.p. 115–116° C.

23. (cis)-4-(2,3-Dihydro-7-methoxybenzofuran-2-spiro-1'-cyclopentan-4-yl)-2-[2-(7-purinyl)ethyl]-4a-5,8,8a-tetrahydro-2H-phthalazin-1-one Prepared from purine and compound 18 as described for compound 22. Crystallized from methanol. M.p. 171–173° C.

24. (cis)-4-(2,3-Dihydro-7-methoxybenzofuran-2-spiro-1'-cyclopentan-4-yl)-2-(p-carboxyphenyl)-4a,5,8,8a-tetrahydro-2H-phthalazin-1-one 20 mmol of compound A, 25 mmol of 4-hydrazinobenzoic acid and 2 g of pyridine hydrochloride were refluxed for 5 h in 50 ml of pyridine. After evaporating the reaction mixture, the residue was dissolved in ethyl acetate and the solution was washed 3 times with 1N hydrochloric acid. The solvent was dried over magnesium sulfate and evaporated. Crystallization from methanol. M. p. 216–219° C.

25. (cis)-4-(2,3-Dihydro-2,2-dimethyl-7-methoxybenzofuran-4-yl)-2-cycloheptyl-4a,5,8,8a-tetrahydro-2H-phthalazin-1-one Prepared from compound 4 and cycloheptyl bromide as described for compound 11. M. p. 114–115° C.

26. (cis)-4-2,3-Dihydro-2,2-dimethyl-7-methoxybenzofuran-4-yl)-2-benzyl-4a,5,8,8a-tetrahydro-2H-phthalazin-1-one Prepared from compound 4 and benzyl bromide as described for compound 11. The compound was purified by chromatography [ethyl acetate/petroleum ether (60–95° C.), 1:6] and crystallized from ethyl acetate/petroleum ether (60–95° C.). M. p. 137–138° C.

27. (cis)-4-(2,3-Dihydro-2,2-dimethyl-7-methoxybenzofuran-4-yl)-2-phenyl-4a,5,8,8a-tetrahydro-2H-phthalazin-1-one Prepared from compound D and phenylhydrazine as described for compound 8. Purified by chromatography [petroleum ether (60–80° C.)/ethyl acetate, 6:1]. Crystallized from diethyl etherlpetroleum ether (60–80° C.). M p. 175° C.

Starting Compounds

A. (cis)-2-(2,3-Dihydro-7-methoxybenzofuran-2-spiro-1'-cyclopentane-4-carbonyl)-1,2,3,6-tetrahydrobenzoic Acid A solution of 35 g of compound E in 350 ml tetrahydrofuran was added slowly to 3.5 g of magnesium in 50 ml of tetrahydrofuran. After complete addition, the mixture was refluxed for 5 hours and left at room temperature for additional 18 hours. This mixture was added slowly to a solution of 18.8 g of (cis)-1,2,3,6-tetrahydrophthalic anhydride in tetrahydrofuran at 0° C. After complete addition the mixture was refluxed for 6 hours and left at room temperature for additional 18 hours after which the reaction was quenched with ammonium chloride and the solvent removed under reduced pressure. The residue was acidified with concentrated hydrochloric acid and the mixture extracted with ethyl acetate. The organic layer was dried over magnesium sulfate and evaporated. The residue was purified by chromatography (petroleum ether/ethyl acetate/acetic acid, 3:1:0.1). Crystallization from diethyl ether. M. p. 132–135° C.

B. (cis)-2-(2,3-Dihydro-7-methoxybenzofuran-2-spiro-1'-cyclopentane-4-carbonyl) cyclohexan-carboxylic Acid Prepared from compound E and cis-1,2-cyclohexandicarboxylic acid as described for compound A. M. p. 161–163° C.

C. 2-(2,3-Dihydro-7-methoxybenzofuran-2-spiro-1'-cyclopentane-4-carbonyl)benzoic Acid The title compound can be prepared from compound E and phthalic acid anhydride as described for compound A.

D. (cis)-2-(2,3-Dihydro-2,2-dimethyl-7-methoxybenzofuran-4-carbonyl)-1,2,3,6-tetrahydro-benzoic Acid Prepared from compound H and cis-1,2,3,6-tetrahydrophthalic anhydride as described for compound A. M. p. 154–156° C.

E. 4-Bromo-2,3-dihydro-7-methoxybenzofuran-2-spiro-1'-cyclopentane

To a solution of 8.4 g of compound F in 100 ml of absolute toluene is added 9 g Amberlist 15; the mixture is stirred at 100° C. for 10 h. After cooling, the $H^+$-ion exchange resin is filtered off and washed with 100 ml methanol. The combined organic solvents are destined off and the residue is chromatographed on a silica gel column to give 7.4 g of the title compound as a yellow oil. TLC (petrolether/ethyl acetate, 6:4), $R_f$=0.72.

F. 2-Cyclopent-1-enylmethyl-3-hydroxy4-methoxybromobenzene

To a solution of 26.5 g (0.074 mol) methyltriphenylphosphonium bromide in 200 ml of absolute tetrahydrofuran is added dropwise at −89° C. under a nitrogen atmosphere 52.1 ml (0.082 mol) of n-butyllithium. Afterwards the suspension is warmed to −30° C., which leads to the dissolution of the suspension. After cooling once again to −70° C., a solution of 19.2 g (0.067 mol) of compound G in 200 ml of absolute tetrahydrofuran is slowly added under a nitrogen atmosphere. Then the mixture is warmed to −10° C. and stirred at this temperature for 5 days. TLC (petroleum ether/ethyl acetate, 6:4), $R_f$(methylene compound)=0.81.

After warming to room temperature the solid substances are filtered off and the filtrate is washed three times with 200 ml of a half-saturated sodium chloride solution and two times with 200 ml of destined water. The combined organic extracts are dried over sodium sulfate and concentrated. The residue is dissolved in 50 ml of quinoline and stirred at 195–205° C. for 1 h. To the cooled quinoline solution is added 400 ml of ethyl acetate and the mixture is washed four times with 200 ml of 2N hydrochloric acid. The organic layer is dried over sodium sulfate and concentrated. The residue is chromatographed on a silica gel column to give 8.4 g of the title compound as a red-brown oil. TLC (petrolether/ethyl acetate, 6:4), $R_f$=0.65.

G. 4-Methoxy-3-(2-oxocyclopentyloxy) bromobenzene

To a solution of 20 g (0.1 mol) of 3-Hydroxy-4-methoxybromobenzene in 300 ml of absolute dimethylformamide is added 17.7 g (0.15 mol) of 2-Chlorocyclopentanone and 41.4 g (0.3 mol) of potassium carbonate. The solution is stirred at room temperature for 12 h. Afterwards the solid substances are filtered off and the filtrate is concentrated. The residue is dissolved in 500 ml of ethyl acetate and washed three times with 200 ml of destined water. The organic layer is dried over sodium sulfate and concentrated. The residue is chromatographed on a silica gel column to give 21.1 g of the title compound as a brown oil. TLC (petroletherdethyl acetate, 6:4), $R_f$=0.47.

H. 4-Bromo-2,3-dihydro-2,2-dimethyl-7-methoxybenzofuran

Prepared analogously to compound E starting from 3-Hydroxy-4-methoxybromobenzene and 1-chloro-or 1-bromoacetone.

Commercial Utility

The compounds according to the invention have useful pharmacological properties which make them industrially utilizable. As selective cyclic nucleotide phosphodiesterase (PDE) inhibitors (specifically of type 4), they are suitable on the one hand as bronchial therapeutics (for the treatment of airway obstructions on account of their dilating action but also on account of their respiratory rate- or respiratory drive-increasing action) and for the removal of erectile dysfunction on account of their vascular dilating action, but on the other hand especially for the treatment of disorders, in particular of an inflammatory nature, e.g. of the airways (asthma prophylaxis), of the skin, of the intestine, of the eyes, of the CNS and of the joints, which are mediated by mediators such as histamine, PAF (platelet-activating factor), arachidonic acid derivatives such as leukotrienes and prostaglandins, cytokines, interleukins, chemokines, alpha-, beta- and gamma-interferon, tumor necrosis factor (TNF) or oxygen free radicals and proteases. In this context, the compounds according to the invention are distinguished by a low toxicity, a good enteral absorption (high bioavailability), a large therapeutic breadth and the absence of significant side effects.

On account of their PDE-inhibiting properties, the compounds according to the invention can be employed in human and veterinary medicine as therapeutics, where they can be used, for example, for the treatment and prophylaxis of the following illnesses: acute and chronic (in particular inflammatory and allergen-induced) airway disorders of varying origin (bronchitis, allergic bronchitis, bronchial asthma, emphysema, COPD); dermatoses (especially of proliferative, inflammatory and allergic type) such as psoriasis (vulgaris), toxic and allergic contact eczema, atopic eczema, seborrhoeic eczema, Lichen simplex, sunburn, pruritus in the anogenital area, alopecia areata, hypertrophic scars, discoid lupus erythematosus, follicular and widespread pyodermias, endogenous and exogenous acne, acne rosacea and other proliferative, inflammatory and allergic skin disorders; disorders which are based on an excessive release of TNF and leukotrienes, for example disorders of the arthritis type (rheumatoid arthritis, rheumatoid spondylitis, osteoarthritis and other arthritic conditions), disorders of the immune system (AIDS, multiple sclerosis), graft versus host reaction, allograft rejections, types of shock (septic shock, endotoxin shock, gram-negative sepsis, toxic shock syndrome and ARDS (adult respiratory distress syndrome)) and also generalized inflammations in the gastrointestinal region (Crohn's disease and ulcerative colitis); disorders which are based on allergic and/or chronic, immunological false reactions in the region of the upper airways (pharynx, nose) and the adjacent regions (paranasal sinuses, eyes), such as allergic rhinitis/sinusitis, chronic rhinitis/sinusitis, allergic conjunctivitis and also nasal polyps; but also disorders of the heart which can be treated by PDE inhibitors, such as cardiac insufficiency, or disorders which can be treated on account of the tissue-relaxant action of the PDE. inhibitors, such as, for example, erectile dysfunction or colics of the kidneys and of the ureters in connection with kidney stones. In addition, the compounds of the invention are useful in the treatment of diabetes insipidus and conditions associated with cerebral metabolic inhibition, such as cerebral senility, senile dementia (Alzheimer's disease), memory impairment associated with Parkinson's disease or multiinfarct dementia; and also illnesses of the central nervous system, such as depressions or arteriosclerotic dementia.

The invention further relates to a method for the treatment of mammals, including humans, which are suffering from one of the above-mentioned illnesses. The method is characterized in that a therapeutically active and pharmacologically effective and tolerable amount of one or more of the compounds according to the invention is administered to the ill mammal.

The invention further relates to the compounds according to the invention for use in the treatment and/or prophylaxis of illnesses, especially the illnesses mentioned.

The invention also relates to the use of the compounds according to the invention for the production of medicaments which are employed for the treatment and/or prophylaxis of the illnesses mentioned.

The invention furthermore relates to medicaments for the treatment and/or prophylaxis of the illnesses mentioned, which contain one or more of the compounds according to the invention.

Additionally, the invention relates to an article of manufacture, which comprises packaging material and a pharmaceutical agent contained within said packaging material, wherein the pharmaceutical agent is therapeutically effective for antagonizing the effects of the cyclic nucleotide phosphodiesterase of type 4 (PDE4), ameliorating the symptoms of an PDE4-mediated disorder, and wherein the packaging material comprises a label or package insert which indicates that the pharmaceutical agent is useful for preventing or treating PDE4-mediated disorders, and wherein said pharmaceutical agent comprises one or more compounds of formula I according to the invention. The packaging material, label and package insert otherwise parallel or resemble what is generally regarded as standard packaging material, labels and package inserts for pharmaceuticals having related utilities.

The medicaments are prepared by processes which are known per se and familiar to the person skilled in the art. As medicaments, the compounds according to the invention (=active compounds) are either employed as such, or preferably in combination with suitable pharmaceutical auxiliaries, e.g. in the form of tablets, coated tablets, capsules, suppositories, patches, emulsions, suspensions, gels or solutions, the active compound content advantageously being between 0.1 and 95%.

The person skilled in the art is familiar with auxiliaries which are suitable for the desired pharmaceutical formulations on account of his expert knowledge. In addition to solvents, gel formers, ointment bases and other active compound excipients, for example antioxidants, dispersants, emulsifiers, preservatives, solubilizers or permeation promoters, can be used.

For the treatment of disorders of the respiratory tract, the compounds according to the invention are preferably also administered by inhalation. To do this, these are either administered directly as a powder (preferably in micronized form) or by atomizing solutions or suspensions which contain them. With respect to the preparations and administration forms, reference is made, for example, to the details in European Patent 163 965.

For the treatment of dermatoses, the compounds according to the invention are in particular administered in the form of those medicaments which are suitable for topical application. For the production of the medicaments, the compounds according to the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The medicaments according to the invention are prepared by processes known per se. The dosage of the active compounds is carried out in the order of magnitude customary for PDE inhibitors. Topical application forms (such as ointments) for the treatment of dermatoses thus contain the active compounds in a concentration of, for example, 0.1–99%. The dose for administration by inhalation is customarily between 0.1 and 3 mg per day. The customary dose in the case of systemic therapy (p.o. or i.v.) is between 0.03 and 3 mg/kg per day.

Biological Investigations

In the investigation of PDE 4 inhibition on the cellular plane, the activation of inflammatory cells is ascribed particular importance. An example is FMLP (N-formyl-methionyl-leucyl-phenylalanine)-induced superoxide production of neutrophilic granulocytes, which can be measured as luminol-amplified chemiluminescence. (Mc Phail LC, Strum SL, Leone PA and Sozzani S, The neutrophil respiratory burst mechanism. In "Immunology Series" 57: 47–76, 1992; ed. Coffey RG (Marcel Decker, Inc., New York-Basel-Hong Kong)).

Substances which inhibit chemiluminescence and cytokine secretion and the secretion of proinflammatory mediators on inflammatory cells, in particular neutrophilic and eosinophilic granulocytes, T-lymphocytes, monocytes and macrophages are those which inhibit PDE 4. This isoenzyme of the phosphodiesterase families is particularly represented in granulocytes. Its inhibition leads to an increase in the intracellular cyclic AMP concentration and thus to the inhibition of cellular activation. PDE 4 inhibition by the substances according to the invention is thus a central indicator for the suppression of inflammatory processes. (Giembycz Mass., Could isoenzyme-selective phosphodiesterase inhibitors render bronchodilatory therapy redundant in the treatment of bronchial asthma?. Biochem Pharmacol 43: 2041–2051, 1992; Torphy TJ et al., Phosphodiesterase inhibitors: new opportunities for treatment of asthma. Thorax 46: 512–523, 1991; Schudt C et al., Zardaverine: a cyclic AMP PDE 3/4 inhibitor. In "New Drugs for Asthma Therapy", 379402, Birkhäiuser Verlag Basel 1991; Schudt C et al., Influence of selective phosphodiesterase inhibitors on human neutrophil functions and levels of cAMP and Ca; Naunyn-Schmiedebergs Arch Pharmacol 344; 682–690, 1991; Tenor H and Schudt C, Analysis of PDE isoenzyme profiles in cells and tissues by pharmacological methods. In "Phophodiesterase Inhibitors", 21–40, "The Handbook of Immunopharmacology", Academic Press, 1996; Hatzelmann A et al., Enzymatic and functional aspects of dual-selective PDE3/4-lnhibitors. In "Phosphodiesterase Inhibitors", 147–160, "The Handbook of Immunopharmacology", Academic Press, 1996.

Inhibition of PDE 4 Activity

Methodology

The activity test was carried out according to the method of Bauer and Schwabe, which was adapted to microtitre plates (Naunyn-Schmiederberg's Arch. Pharmacol. 311, 193–198, 1980). In this test, the PDE reaction is carried out in the first step. In a second step, the resultant 5'-nucleotide is cleaved to the uncharged nucleoside by a snake venom 5'-nucleotidase from Crotalus Atrox. In the third step, the nucleoside is separated from the remaining charged substrate on ion exchange columns. The columns are eluted directly into minivials using 2 ml of 30 mM ammonium formate (pH 6.0), to which a further 2 ml of scintillation fluid is added for counting.

The inhibitory values determined for the compounds according to the invention follow from the following table A, in which the numbers of the compounds correspond to the numbers of the examples.

TABLE A

| Inhibition of PDE4 activity [measured as $-\log IC_{50}$ (mol/l)] ||
| Compound | $-\log IC_{50}$ |
| --- | --- |
| 1 | 8.02 |
| 5 | 9.22 |
| 6 | 9.17 |
| 7 | 8.93 |
| 8 | 8.87 |
| 9 | 7.80 |
| 11 | 7.66 |
| 12 | 8.22 |
| 13 | 9.22 |
| 14 | 8.62 |
| 17 | 8.36 |
| 22 | 8.82 |
| 24 | 9.38 |
| 25 | 9.01 |
| 26 | 8.72 |
| 27 | 8.74 |

What is claimed is:

1. A compound of formula I,

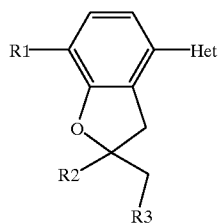

(I)

in which
R1 is 1–4C-alkoxy, 3–5C-cycloalkoxy, 3–5C-cycloalkylmethoxy, or 1–4C-alkoxy which is completely or predominantly substituted by fluorine,
R2 is 1–4C-alkyl and
R3 is hydrogen or 1–4C-alkyl,
or wherein
R2 and R3 together and with inclusion of the two carbon atoms, to which they are bonded, form a spirolinked 5-, 6- or 7-membered hydrocarbon ring, optionally interrupted by an oxygen or sulphur atom,
Het represents a heterocycle having the meaning

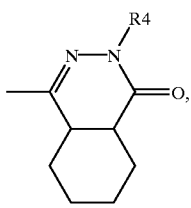

(a)

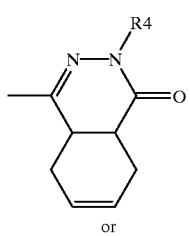

(b)

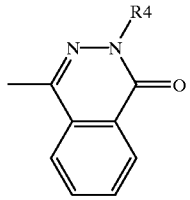

(c)

wherein
R4 is R5, —$C_mH_{2m}$—R6 or —$C_pH_{2p}$—Y—Ar
R5 is hydrogen, 1–8C-alkyl, 3–10C-cycloalkyl, 3–7C-cycloalkylmethyl, 7–10C-polycycloalkyl, an unsubstituted phenyl or pyridyl radical or a phenyl radical substituted by R51 and/or R52, in which
R51 is 1–4C-alkyl, 1–4C-alkoxy, carboxyl, 1–4C-alkoxycarbonyl, cyano, nitro, halogen, hydroxyl, amino, mono- or di-1–4C-alkylamino, imidazolyl or tetrazolyl, and R52 is 1–4C-alkyl, 1–4C-alkoxy, nitro or halogen,
R6 is hydroxyl, halogen, nitro, cyano, carboxyl, 1–4C-alkoxycarbonyl, amino, mono or di-1–4C-alkylamino, aminocarbonyl or mono- or di-1–4C-alkylaminocarbonyl,
Y is O (oxygen), S (sulphur) or a covalent bond,
Ar is an unsubstituted phenyl, naphthyl, pyridyl, pyrazinyl, pyridazinyl, pyrimidinyl, quinazolinyl, quinoxalinyl, cinnolinyl, isoquinolyl, quinolyi, purinyl, benzimidazolyl, benzotriazolyl, benzoxazolyl, coumarinyl, imidazolyl, pyrazolyl, oxazolyl or pyrrotyl radical or a phenyl radical substituted by R7 and/or R8, in which
R7 is hydroxyl, halogen, nitro, cyano, 1–4C-alkyl, 1–4C-alkoxy, carboxyl, carboxy-1–4C-alkyl, 1–4C-alkoxycarbonyl, amino, mono- or di-1–4C-alkylamino, aminocarbonyl, mono- or di-1–4C-alkyl-aminocarbonyl, 1–4C-alkylcarbonylamino, imidazolyl or tetrazolyl,
R8 is halogen, nitro, 1–4C-alkyl or 1–4C-alkoxy,
m is an integer from 1 to 4,
p is an integer from 1 to 4, or a salt thereof.

2. A compound of formula I according to claim 1, in which

R1 is 1–4C-alkoxy, 3–5C-cycloalkoxy, 3–5C-cycloalkylmethoxy, or 1–4C-alkoxy which is completely predominantly substituted by fluorine,
R2 is 1–4C-alkyl and
R3 is hydrogen or 1–4C-alkyl,
or wherein
R2 and R3 together and with inclusion of the two carbon atoms, to which they are bonded, form a spirolinked cyclopentane, cyclohexane, tetrahydrofuran or tetrahydropyran ring,
Het represents a heterocycle having the meaning

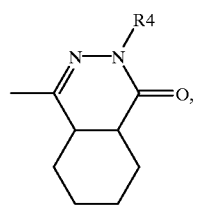

(a)

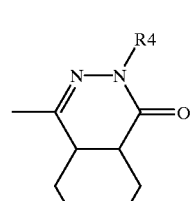

(b)

-continued

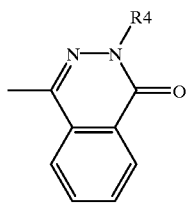
(c)

wherein

R4 is R5, —$C_mH_{2m}$—R6 or —$C_pH_{2p}$—Y—Ar,

R5 is hydrogen, 1–6C-alkyl, 3–7C-cycloalkyl, 3–7C-cycloalkylmethyl, bornyl, norbornyl, adamantyl or an unsubstituted or by R51 substituted phenyl radical, in which R51 is 1–4C-alkyl, 1–4C-alkoxy, carboxyl, 1–4C-alkoxycarbonyl or halogen, R6 is hydroxyl, halogen, carboxyl or 1–4C-alkoxycarbonyl, Y is O (oxygen) or a covalent bond, Ar is an unsubstituted phenyl, pyridyl, purinyl, benzimidazolyl, benzotriazolyl, imidazolyl, pyrazolyl, or pyrrolyl radical, or a phenyl radical substituted by R7, in which R7 is halogen, nitro, cyano, 1–4C-alkyl, 1–4C-alkoxy, carboxyl, carboxy-1–2C-alkyl, 1–4C-alkoxy-carbonyl or tetrazolyi, m is an integer from 1 to 4, p is an integer from 1 to 4, or a salt thereof.

3. A compound of formula I according to claim 1, in which

R1 is 1–2C-alkoxy or 1–2C-alkoxy which is completely or predominantly substituted by fluorine, R2 is 1–4C-alkyl and R3 is hydrogen or 1–4C-alkyl, or wherein R2 and R3 together and with inclusion of the two carbon atoms, to which they are bonded, form a spirolinked cyclopentane or cyclohexane ring, Het represents a heterocycle having the meaning

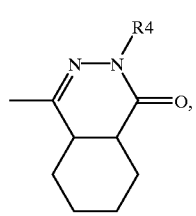
(a)

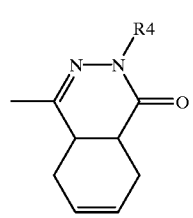
(b)

or

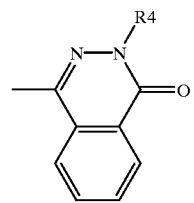
(c)

wherein

R4 is R5, —$C_mH_{2m}$—R6 or —$C_pH_{2p}$—Y—Ar,

R5 is hydrogen, 3–7C-cycloalkyl, 3–7C-cycloalkylmethyl, adamantyl or an unsubstituted or by R51 substituted phenyl radical, in which R51 is carboxyl or 1–4C-alkoxycarbonyl, R6 is hydroxyl or halogen, Y is O (oxygen) or a covalent bond, Ar is an unsubstituted phenyl, pyridyl, imidazolyl or purinyl radical, or a phenyl radical substituted by R7, in which R7 is cyano, 1–4C-alkyl, 1–4C-alkoxy, carboxyl, 1–4C-alkoxycarbonyl or tetrazolyl, m is an integer from 1 to 4, p is an integer from 1 to 4, or a salt thereof.

4. A compound of formula I according to claim 1, in which

R1 is methoxy or difluoromethoxy,

R2 is methyl,

R3 is hydrogen, or wherein

R2 and R3 together and with inclusion of the two carbon atoms, to which they are bonded, form a spirolinked cyclopentane ring, Het represents a heterocycle having the meaning

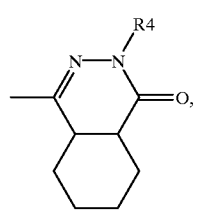
(a)

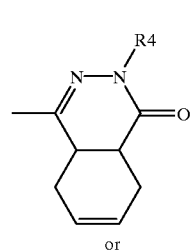
(b)

or

-continued

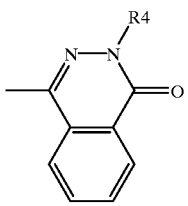

(c)

wherein

R4 is R5, —C$_m$H$_{2m}$—R6 or —C$_p$H$_{2p}$—Y—Ar,

R5 is hydrogen, 3–7C-cycloalkyl or an unsubstituted or by R51 substituted phenyl radical, in which R51 is carboxyl, R6 is hydroxyl or halogen, Y is O (oxygen) or a covalent bond, Ar is an unsubstituted phenyl, pyridyl, imidazolyl or purinyl radical, or a phenyl radical substituted by R7, in which R7 is cyano, carboxyl or tetrazolyl, m is an integer from 1 to 4, p is an integer from 1 to 4, or a salt thereof.

5. A compound of formula I according to claim 1, in which

R1 is methoxy,

R2 is methyl,

R3 is hydrogen, or wherein

R2 and R3 together and with inclusion of the two carbon atoms, to which they are bonded, form a spirolinked cyclopentane ring, Het represents a heterocycle having the meaning

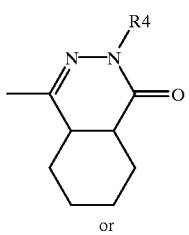

(a)

or

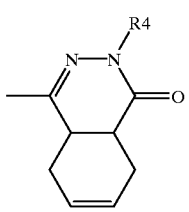

(b)

wherein

R4 is R5, —C$_m$H$_{2m}$—R6 or —C$_p$H$_{2p}$—Y—Ar,

R5 is hydrogen, cyclopentyl, cycloheptyl, phenyl or p-carboxyphenyl,

R6 is hydroxyl,

Y is O (oxygen) or a covalent bond,

Ar is an unsubstituted phenyl, pyridyl, imidazolyl or purinyl radical, or a phenyl radical substituted by R7, in which R7 is cyano, carboxyl or tetrazoyl, m is an integer from 1 to 4, p is an integer from 1 to 4, or a salt thereof.

6. A compound according to claim 1, wherein Het represents a heterocycle having the meaning

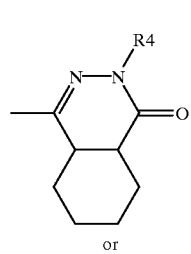

(a)

or

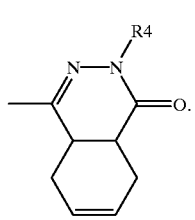

(b)

or a salt thereof.

7. A medicament composition containing one or more compounds according to claim 1 together with a usual pharmaceutical auxiliary and/or carrier.

8. A method of treating a disorder amenable to treatment with a selective cyclic nucleotide phosphodiesterase inhibitor of type 4 (PDE 4), which comprises administering an effective amount of a compound of claim 1, or a pharmaceutically acceptable salt thereof, to a subject afflicted with such disorder.

9. A method of claim 8 wherein the disorder is an airways disorder.

10. A method of claim 8 wherein the disorder is a dermatosis.

11. A method of preparing a medicament composition which comprises combining an effective amount of a selective cyclic nucleotide phosphodiesterase inhibitor of type 4 (PDE 4) with a pharmaceutical auxiliary and/or carrier, wherein the selective cyclic nucleotide phosphodiesterase inhibitor of type 4 is a compound of claim 1 or a pharmacologically acceptable salt thereof.

* * * * *